United States Patent
Grise

(10) Patent No.: US 7,163,506 B2
(45) Date of Patent: Jan. 16, 2007

(54) DEVICE FOR THE TREATMENT OF URINARY INCONTINENCE

(75) Inventor: Philippe Grise, Bihorel (FR)

(73) Assignee: Centre Hospitalier Universitaire de Rouen, Rouen (FR)

( * ) Notice: Subject to any disclaimer, the term of this patent is extended or adjusted under 35 U.S.C. 154(b) by 0 days.

(21) Appl. No.: 10/413,470

(22) Filed: Apr. 15, 2003

(65) Prior Publication Data

US 2003/0199729 A1    Oct. 23, 2003

(30) Foreign Application Priority Data

Apr. 17, 2002   (FR) .................................. 02 04796

(51) Int. Cl.
*A61F 2/00* (2006.01)
(52) U.S. Cl. .......................................... 600/30; 600/37
(58) Field of Classification Search ............ 600/29–31, 600/37; 128/DIG. 25; 606/139, 151–158
See application file for complete search history.

(56) References Cited

U.S. PATENT DOCUMENTS

| 4,549,531 A | 10/1985 | Trick |
| 4,786,276 A | 11/1988 | Haber |
| 5,518,504 A * | 5/1996 | Polyak .................... 623/14.13 |
| 6,117,067 A * | 9/2000 | Gil-Vernet .................. 600/30 |
| 6,221,005 B1 * | 4/2001 | Bruckner et al. ............. 600/30 |

FOREIGN PATENT DOCUMENTS

| EP | 0 941 712 | 9/1999 |
| WO | WO 98 31301 | 7/1998 |
| WO | WO 00 66030 | 11/2000 |

* cited by examiner

*Primary Examiner*—John P. Lacyk
(74) *Attorney, Agent, or Firm*—Young & Thompson

(57) ABSTRACT

Constitution of a suburethral sling connected to two balloons located on each side of the urethra. The device preferably consists of two subassemblies (12a and 12b) each comprising an inflatable balloon (13) and a strip (16) one end of which is attached to the surface of the balloon. The two strips (16) are connected together to form a suburethral sling.

20 Claims, 1 Drawing Sheet

DEVICE FOR THE TREATMENT OF URINARY INCONTINENCE

BACKGROUND OF THE INVENTION

The invention concerns a device for the treatment of urinary incontinence, in particular stress incontinence (due to coughing, walking, etc.) in women. The device according to the invention can be implanted by means of a new non-traumatic surgical procedure.

Urinary incontinence in women can result from a lack of support in the cervico-urethral area, sometimes associated with an insufficiency of the urethral sphincter. Several surgical procedures have been proposed to prevent such incontinence. Among the most efficacious of these known methods is a suburethral support in the form of a band designed to lift the urethra, which is implanted via a small vaginal incision. This tape, or sling, is attached to a needle that the surgeon engages in the pelvic aponeurosis. The sling is then tunneled from one side of the urethra to the other, under the bladder, and the surgeon brings out the needle through the lower part of the anterior abdominal wall.

This method has two drawbacks, however. The first is a risk of perforation of the bladder during the operation. The second, post-operatively, is the risk of excessive tension of the sling, hindering urination. The tension is difficult to set during the operation, and cannot be adjusted afterwards. In some cases a second operation is necessary to release the tension of the sling.

Another method is to introduce small inflatable sacs or balloons on each side of the urethra. Each balloon has a valve and is inflated in situ. It is fitted by means of an insertion system consisting of a sheath, a needle and a catheter.

SUMMARY OF THE INVENTION

The present invention is a combination of these two methods that provides, in particular, a solution to the problem of regulating the tension in the suburethral sling. The principle of the invention is to fit a suburethral sling connected to two balloons located on each side of the urethra.

So the invention proposes a device for the treatment of the urinary incontinence, in particular in women, comprising a suburethral sling suspended by attachments to two fastening points made of two balloons adapted to be located on either side of a bladder neck or urethra.

Preferably, the invention proposes a device for the treatment of urinary incontinence, characterized in that it comprises two subassemblies designed to be connected together, wherein each subassembly comprises an inflatable balloon equipped with a valve and a strip attached to the surface of said balloon, the strips of the two balloons being designed to be connected together to form a suburethral sling.

When the two subassemblies are installed and the two strips are joined end to end, to form a sling to lift the urethra, it is easy to adjust the tension of said sling by inflating and deflating the two balloons appropriately. The strips are for example assembled using sutures on one side of the urethra. The balloons can be inflated by filling them with physiological saline.

As known to prior art, each balloon is preferably fitted with a valve. The valve can be attached directly to the balloon. If the possibility of post-operative adjustment is wanted, then a variant known in prior art can be used, whereby said valve is connected to the balloon via a conduit. This allows subcutaneous positioning of the valve, and so enables post-operative intervention to adjust, if necessary, the inflation of said balloon.

The balloon and the strip are made of an appropriate biocompatible material (biomaterial). Preferably, the balloon is made of silicone; similarly, the strip is advantageously made of flexible synthetic material, preferably polypropylene. The strip preferably comprises a braiding with a loose mesh or, as an alternative, a flat surface comprising pores, to facilitate tissue incorporation. The balloon can be of roughly spherical or roughly ovoid shape.

BRIEF DESCRIPTION OF THE DRAWINGS

The invention will be more readily understood, and the other advantages that it has will be more evident in the following description, given solely as a example, and which refers to the appended drawings, where.

DETAILED DESCRIPTION OF THE PREFERRED EMBODIMENTS

Figure 1:
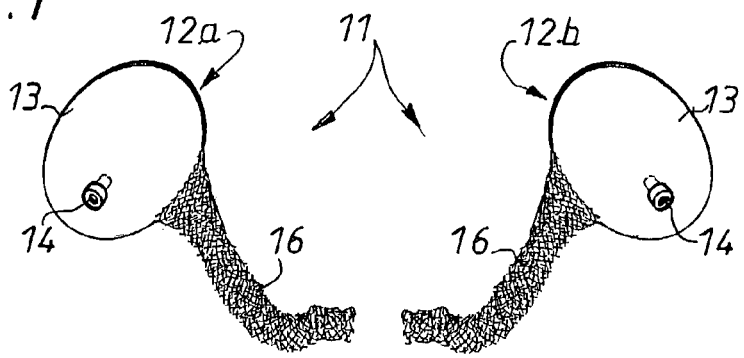
FIG. 1 discloses a device made of two subassemblies, before assembly of their strips, FIG. 2 discloses a subassembly according to a possible variant, and, FIG. 3 is a diagram showing the implantation of the device on each side of the urethra.
Figure 2:
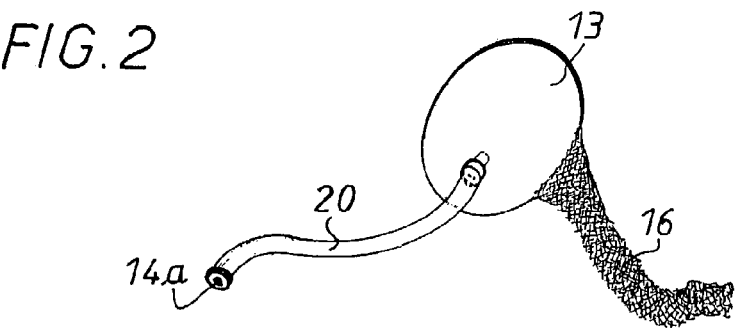

With particular reference to FIG. 1, it can be seen that device 11 of the invention, according to a preferred embodiment, is composed of two similar subassemblies 12a and 12b each comprising an inflatable balloon 13 equipped with a valve 14 and a strip 16, one end of which is attached to the surface of said balloon. The two strips 16 are designed to be connected together during the surgical operation to form a suburethral sling. In the example of FIG. 1, the valve 14 is attached directly to the balloon 13. The latter is made of silicone in the example. It is roughly spherical, and when it is filled, for example with physiological saline, its diameter is about 1 cm. The balloon can also be roughly ovoid in shape, with approximately the same dimensions. Each strip 16 can be made of polypropylene or any other flexible synthetic material. It is preferably braided with a loose mesh for the reason stated above. In the example of FIG. 2, the valve 14a is connected to the balloon by a conduit 20 for subcutaneous positioning of the valve, which, as known in prior art, enables the inflation of the balloon to be adjusted, so obviating further surgery.

Figure 3:
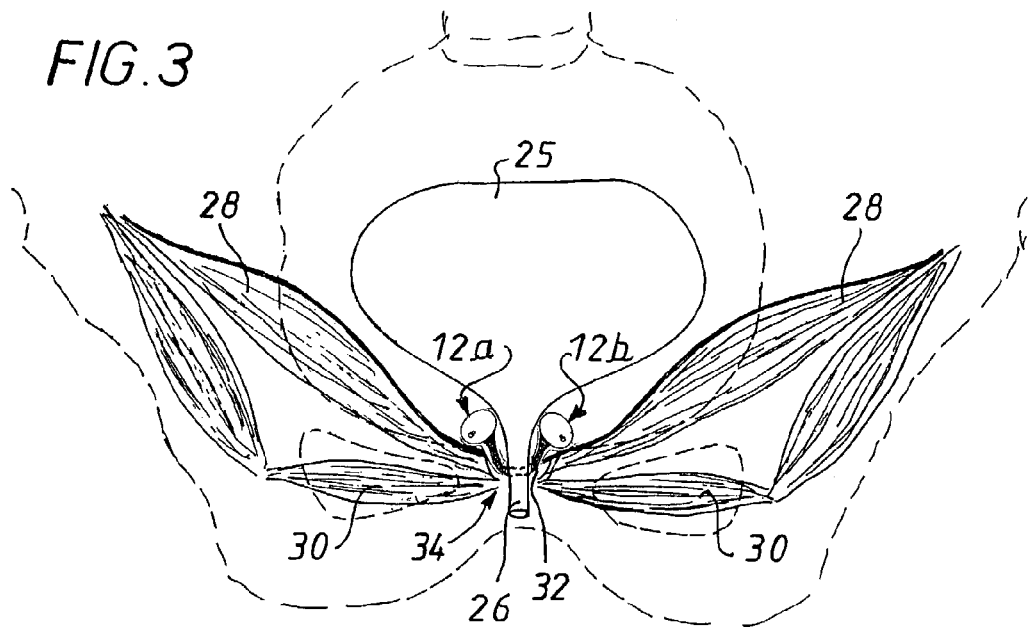

We now describe the surgical implantation of the device. FIG. 3 depicts the bladder 25 and its prolongation, the urethra 26. The purpose of the surgery is to 'lift' the urethra by installing a suburethral sling anchored to the two balloons 12a and 12b placed on each side of the urethra below the bladder. On each side of the bladder and urethra are shown the pelvic aponeurosis 28 and the transverse muscle of the perineum 30. The surgeon makes a small vaginal incision to gain access to the distal part of the urethra. The pelvic aponeurosis is then perforated using a round-ended instrument. A sheath is slipped on this instrument, and a subassembly 12a and 12b (sac or balloon not inflated) is inserted through this sheath and positioned under the bladder on one side of the urethra. The sac or balloon is then inflated. When the two subassemblies 12a and 12b have been positioned on each side of the urethra, the strips 16 are connected together (junction 32) using sutures, staples or a clip, on one side of the urethra. A suburethral sling 34 is thereby formed between the two balloons. The vaginal incision is then closed.

This operating procedure eliminates the risk of perforating the bladder. The advantages of the invention are as follows. During surgery the balloons are positioned on each side of the urethra, i.e., below the lateral surfaces of the bladder, which eliminates the risk of perforating it. The tension of the sling can be regulated during surgery by suturing the strips together to give the sling the right length according to the tension required. If necessary, the sling can be slackened by deflating one or both balloon(s) by simply draining off saline. In addition, the balloons strengthen the pelvic aponeurosis, the possible weakness of which contributes to the lack of support of the bladder and so partly accounts for the incontinence. At rest, the balloons do not exert any significant side pressure on the urethra. However, during an abdomino-pelvic pressure effort the sling pulls the balloons together, thus enhancing their occlusive effect on the urethra.

It will be appreciated that the invention thus proposes a device for the treatment of urinary incontinence in women comprising a suburethral sling suspended by attachments to two fastening points made of two little balloons of simple shape, easy to implant on either side of the bladder neck (urethra) and allowing at the same time the fastening of the sling and the adjusting of same, easy to be used per operatively or post-operatively. The balloon is not secured to any fixed part and contributes by its presence to a reinforcement of a possible weakness of the pelvic fascia, and provides, during coughing or abdominal hyperpressure, a dynamic effect intended to act on the tension of the sling and on the bladder neck.

Each balloon-strip assembly is easy to put in place.

The invention claimed is:

1. A device for the treatment of urinary incontinence comprising a suburethral sling suspended between two freely movable and independently inflatable balloons to be located on either side of an urethra.

2. The device of claim 1, wherein at least one of said two inflatable balloons is equipped with a valve.

3. The device according to claim 2, wherein said valve is directly attached to said one of said two balloons.

4. The device of claim 2, wherein said valve is connected to said one of said two balloons by a conduit for allowing a subcutaneous positioning of said valve.

5. The device of claim 1, wherein said sling comprises a strip made of a flexible synthetic material, which is braided with a loose mesh.

6. The device of claim 5, wherein said strip is made of polypropylene.

7. The device of claim 1, wherein at least one of said two balloons is made of silicone.

8. The device of claim 5, wherein at least one of said two balloons is made of silicone.

9. The device of claim 1, wherein at least one of said two balloons is substantially spherical in shape.

10. The device of claim 1, wherein at least one of said two balloons is substantially ovoid in shape.

11. A device for the treatment of urinary incontinence comprising two subassemblies designed to be connected together, each subassembly comprising an inflatable balloon and a strip attached to a surface of said inflatable balloon, the strips of said two assemblies being designed to be connected together to form a suburethral sling suspended to said balloons, said balloons being adapted and arranged to be freely positionable on either side of an urethra.

12. The device of claim 11, wherein at least one of said two balloons is inflatable and equipped with a valve.

13. The device of claim 12, wherein said valve is directly attached to said one of said two balloons.

14. The device of claim 12, wherein said valve is connected to said one of said two balloons by a conduit for allowing a subcutaneous positioning of said valve.

15. The device of claim 11, wherein said sling comprises a strip made of a flexible synthetic material, which is braided with a loose mesh.

16. The device of claim 15, wherein aid strip is made of polypropylene.

17. The device of claim 11, wherein at least one of said two balloons is made of silicone.

18. The device of claim 11, wherein at least one of said two balloons is substantially spherical in shape.

19. The device of claim 11, wherein at least one of said two balloons is substantially ovoid in shape.

20. A device for the treatment of urinary incontinence comprising two subassemblies designed to be connected together, each subassembly comprising an inflatable balloon and a material strip directly connected to a surface of said balloon, said strip of each of said two subassemblies being connected together to form a suburethral sling suspended between a respective said balloon, each said balloon being freely positionable on either side of an urethra, without being secured to any fixed part.

* * * * *